US008105983B2

(12) United States Patent
Kim et al.

(10) Patent No.: US 8,105,983 B2
(45) Date of Patent: Jan. 31, 2012

(54) HIGH-THROUGHPUT METHOD FOR OPTIMUM SOLUBILITY SCREENING FOR HOMOGENEITY AND CRYSTALLIZATION OF PROTEINS

(75) Inventors: Sung-Hou Kim, Moraga, CA (US); Rosalind Kim, Moraga, CA (US); Jamila Jancarik, Walnut Creek, CA (US)

(73) Assignee: The Regents of the University of California, Oakland, CA (US)

( * ) Notice: Subject to any disclaimer, the term of this patent is extended or adjusted under 35 U.S.C. 154(b) by 764 days.

(21) Appl. No.: 11/393,209

(22) Filed: Mar. 29, 2006

(65) Prior Publication Data

US 2006/0223120 A1    Oct. 5, 2006

Related U.S. Application Data

(60) Provisional application No. 60/666,738, filed on Mar. 29, 2005.

(51) Int. Cl.
*C40B 30/10*    (2006.01)
(52) U.S. Cl. .................... 506/12; 506/7; 702/22; 702/23
(58) Field of Classification Search .................... 506/12, 506/7; 702/22, 23, 19
See application file for complete search history.

(56) References Cited

U.S. PATENT DOCUMENTS

2007/0144973 A1 *    6/2007    Tsonev et al. ................. 210/659

FOREIGN PATENT DOCUMENTS

WO    WO2006074178    *    7/2006

OTHER PUBLICATIONS

Collins et al., "A Preliminary Solubility Screen Used to Improve Crystallization Trials: Crystallization and Preliminary X-ray Structure Determination of Aeropyrum Pernix Flap Endonuclease-I," Acta Crystallography Section D, vol. 60 (No. 9), p. 1674-1678, (Sep. 2004).
D'Arcy, "Crystallizing Proteins—a Rational Approach?," Acta Crystallography Section D, vol. 50 (No. 4), p. 469-471, (Jul. 1994).
Ferre-D'Amare, "Dynamic Light Scattering in Evaluating Crystallizability of Macromolecules," Methods in Enzymology, vol. 276, p. 157-166, (1997).
Habel et al., "Dynamic Light-Scattering Analysis of Full-length Human RPA14/32 Dimer: Purification, Crystallization and Self-Association," Acta Crystallography Section D, vol. 57 (No. 2), p. 254-259, (Feb. 2001).
Jancarik et al., "Sparse Matrix Sampling: A Screening Method for Crystallization of Proteins," Journal of Applied Cyrstallography, vol. 24 (No. 4), p. 409-411, (Aug. 1991).
Lepre et al., "Microdrop Screening: A Rapid Method to Optimize Solvent Conditions for NMR Spectroscopy of Proteins," Journal of Biomolecular NMR, vol. 12 (No. 4), p. 493-499, (Nov. 1998).
Zulauf et al., "Light Scattering of Proteins as a Criterion for Crystallization," Journal of Crystal Growth, vol. 122, p. 102-106, (1992).

* cited by examiner

*Primary Examiner* — T. D. Wessendorf
(74) *Attorney, Agent, or Firm* — Michelle Chew Wong; Lawrence Berkeley National Laboratory (57) ABSTRACT

An optimum solubility screen in which a panel of buffers and many additives are provided in order to obtain the most homogeneous and monodisperse protein condition for protein crystallization. The present methods are useful for proteins that aggregate and cannot be concentrated prior to setting up crystallization screens. A high-throughput method using the hanging-drop method and vapor diffusion equilibrium and a panel of twenty-four buffers is further provided. Using the present methods, 14 poorly behaving proteins have been screened, resulting in 11 of the proteins having highly improved dynamic light scattering results allowing concentration of the proteins, and 9 were crystallized.

5 Claims, 6 Drawing Sheets

FIG. 2A

Step 1: Optimum Solubility Screen

List of optimization buffers
Table 1

| | Buffers (100mM) | pH |
|---|---|---|
| 1 | Glycine | 3 |
| 2 | Citric Acid | 3.2 |
| 3 | PIPPS | 3.7 |
| 4 | Citric Acid | 4 |
| 5 | Sodium acetate | 4.5 |
| 6 | Na K phosphate | 5 |
| 7 | Sodium citrate | 5.5 |
| 8 | Na K phosphate | 6 |
| 9 | Bis Tris | 6 |
| 10 | MES | 6.2 |
| 11 | ADA | 6.5 |
| 12 | Bis Tris Propane | 6.5 |
| 13 | Cacodylate | 6.5 |
| 14 | Ammonium acetate | 7 |
| 15 | MOPS | 7 |
| 16 | Na K phosphate | 7 |
| 17 | HEPES | 7.5 |
| 18 | TRIS | 7.5 |
| 19 | EPPS | 8 |
| 20 | Imidazole | 8 |
| 21 | TRIS | 8.5 |
| 22 | CHES | 9 |
| 23 | CHES | 9.5 |
| 24 | CAPS | 10 |

Linbro Plate

Step 2: Additive Screen

Test additives using best buffer:
25, 50, 100 mM NaCl
5 and 10% glycerol
2 mM CHAPS (CMC=6 to 10 mM)
0.1%, 1% Octylglucoside (CMC=0.53%)
0.1%, 1% Dodecyl Maltoside (CMC=0.0087%)
30mM TCEP, 5mM DTT, 10 mM β-mercaptoethanol Two hour incubation

→

Perform DLS
Pick best additive, exchange protein into optimal buffer/additive
Set up Crystal Screens

1371B in 100 mM Tris, pH 8.5
1% Octylglucoside

C

Crystals of 1371B
Structure solved

D

HIGH-THROUGHPUT METHOD FOR OPTIMUM SOLUBILITY SCREENING FOR HOMOGENEITY AND CRYSTALLIZATION OF PROTEINS

CROSS-REFERENCE TO RELATED APPLICATIONS

This application claims the benefit of priority to U.S. Provisional Patent Application No. 60/666,738, filed on Mar. 29, 2005, which is hereby incorporated by reference.

BACKGROUND OF THE INVENTION

1. Field of the Invention

The present invention relates to high throughput methods for screening for optimal solution conditions for crystallizing proteins.

2. Related Art

Advances in X-ray crystallography have provided three-dimensional structures of thousands of proteins. In spite of these advances, protein aggregation continues to be a common problem that can lead to unsuccessful crystallization of proteins. This problem is becoming more prominent in attempts at crystallizing many different proteins and protein complexes in a structural genomics scale.

At the Berkeley Structural Genomics Center (BSGC), a purified protein sample is obtained after one or more chromatography steps (immobilized metal affinity chromatography (IMAC), ion-exchange chromatography, and size exclusion chromatography), and the sample is analyzed by sodium dodecyl sulfate-polyacrylamide gel electrophoresis (SDS-PAGE) (Laemmli, 1971) to determine the chemical purity of the protein. In the process of developing techniques to automate protein purification, one tries as much as possible to use a set of generic buffers. Very little is known about the properties of the proteins a priori, except for theoretical pI, molecular weight and amino acid composition. The general practice is to use one or two favorite buffers where pH and salt concentration are some of the variables. However, a protein has complex properties and its condition and behavior depend very much on the environment surrounding it. In the past when faced with difficulties of aggregation and precipitation, one would try to change purification parameters, add or remove fusion tags, test some additives (e.g., DTT, glycerol, etc.). After purification, the protein is concentrated and the presence of aggregates is assessed using for example, the dynamic light scattering method. This method as described by Zulauf & D'Arcy (1992) has shown that the presence of aggregates in the protein solution may inhibit crystal nucleation or growth (Habel et al., 2001, Ferre-D'Amare & Burley, 1997).

In order to grow crystals, one must identify the conditions under which proteins will precipitate out of solution. The technique of vapor diffusion is commonly used to analyze this controlled precipitation and by using a sparse matrix approach (Jancarik and Kim, 1991 and further expanded by Hampton Research (Aliso Viejo, Calif.)), one can test a large number of crystallization conditions. This assumes that the starting protein solution is not aggregated or precipitated. In both the preparation for NMR or X-ray crystallography samples, one must start with a protein solution that is homogeneous and monodisperse. Lepre and Moore (1998) developed a modified vapor diffusion method to efficiently screen solvent conditions for NMR samples in order to optimize solubility. Collins et al. have developed preliminary solubility screens using different buffer components and focus on the combination of best anion and cation buffers for solubility improvement (*Acta Cryst.* (2004) D60, 1674-1678).

STATEMENT OF GOVERNMENTAL SUPPORT

This invention was made during work supported by National Institutes of Health GM-62412 and U.S. Department of Energy under Contract No. DE-AC03-76SF00098, now DE-Ac02-05CH11231. The government has certain rights in this invention.

BRIEF SUMMARY OF THE INVENTION

The present invention provides a method of screening for optimal solubilization (OS) conditions to crystallize proteins comprised of the following steps: (1) providing a reservoir buffer in a container, wherein the container has a cover slip; (2) depositing an aliquot of said buffer either on the cover slip or on a pedestal in the container above the buffer reservoir in each container; (3) placing a protein in said aliquot of said buffer to form a protein solution drop; (4) inverting the cover slip onto the container; (5) incubating the container at a given temperature for a sufficient period of time; and (6) evaluating said protein solution drop for solubility and monodispersity. The method for screening is repeated or performed in parallel with a set of at least 4 buffers for each protein provided in order to screen the optimal solubilization conditions. The set of buffers can be comprised of 24 buffers, and in preferred embodiments, the set of 24 buffers is the set in Table 1.

Thus, the present invention further provides for a high-throughput method to screen for optimum solubility condition to crystallize proteins comprising the following steps: (1) providing a set of 24 buffers as shown in Table 1; (2) providing a multi-well container comprised of at least 24 wells, wherein each well has a cover slip; (3) adding each of the 24 buffers to each respective well of said container; (4) depositing on each cover slip or reservoir pedestal, a protein solution drop comprised of an aliquot of the protein and an aliquot of the same buffer in the well; (5) inverting the cover slips onto each respective well; (6) incubating the container at a given temperature for a sufficient period of time; and (7) evaluating any clear protein solution drops to select the optimum solubility condition.

If the protein solution drop is not clear, an aliquot of an additive is added to each protein solution drop to find the best condition. The clear protein solution drops are evaluated to determine the monodispersity of the sample. Therefore, the method can further comprise the step of depositing an aliquot of an additive in the protein solution drop to help screen for the optimum solubility condition.

Herein is described methods to test a panel of buffers and many additives in order to obtain the most homogeneous and monodisperse protein conditions for proteins that aggregate and cannot be concentrated prior to setting up crystallization screens. In a preferred embodiment, a panel of twenty-four buffers is tested using the hanging-drop method and vapor diffusion equilibrium. After monitoring precipitation, the conditions leading to clear drops are selected for dynamic light scattering (DLS) characterization. If the DLS results are not optimal, a series of additives are tested in the presence of the best buffer selected from the initial screen and again DLS is used to determine the best condition. The methods of the invention have been applied to 14 poorly behaving proteins with the results being 11 of the proteins had highly improved DLS results and were able to concentrate well after exchanging buffer, and 9 have crystallized.

DETAILED DESCRIPTION OF THE PREFERRED EMBODIMENT

In order to grow crystals, one must identify the conditions under which proteins will precipitate out of solution. Using the technique of vapor diffusion to analyze this controlled precipitation with a sparse matrix approach (See Jancarik and Kim, 1991 and further expanded by Hampton Research (Aliso Viejo, Calif.)), one can test a large number of crystallization conditions. However, this technique assumes that the starting protein solution is not aggregated or precipitated. For instance, in both the preparation for NMR or X-ray crystallography samples, one must start with a protein solution that is homogeneous and monodisperse.

Herein is described a method to increase the solubility of samples that were badly aggregated or showed precipitation and coupled it with DLS for determining the aggregation state of a given protein sample. This method requires a very small quantity of protein for the initial OS screen and for testing additives. The ease of use of this screen and the capability of testing many conditions, makes this a very efficient means for searching the best solvent condition.

Figure 1:
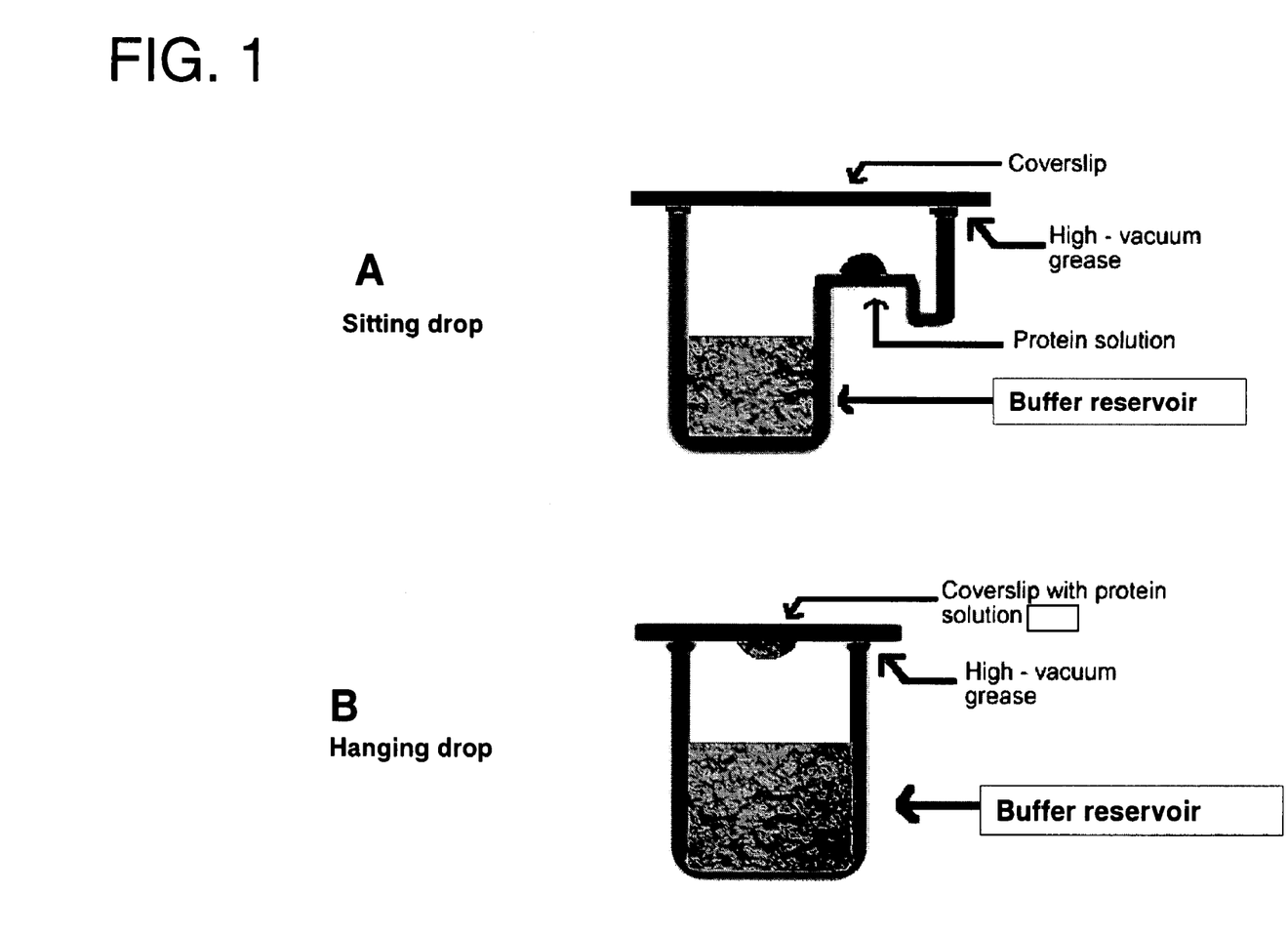
FIG. 1 shows schematics of the two methods of vapor diffusion crystallization: Sitting drop method (A) and Hanging drop method (B).

The present high-throughput method tests a panel of buffers and many additives in order to obtain the most homogeneous and monodisperse protein condition for proteins that aggregate and cannot be concentrated prior to setting up crystallization screens. Referring to FIG. 1, the method can be carried out using the sitting drop or the hanging drop methods of crystallizationl A panel of at least four buffers should be screened for each protein in the method, although it is preferred that more buffers are used in the screening method. This is insure that sufficient number of buffers at a broad range of pH values are used. In a specific preferred embodiment, a panel of twenty-four buffers is tested using the hanging-drop method and vapor diffusion equilibrium.

After monitoring precipitation, the conditions leading to clear drops are selected for DLS characterization. For this part of the screen only 1 μl of protein per well (concentration ranging from 3 mg/ml or higher) are required. If the DLS results are not optimal, a series of additives are tested in the presence of the best buffer selected from the initial screen and again DLS is used to determine the best condition. The examples describe 14 poorly behaving proteins which were tested using the present methods. After screening using the present methods, 11 of the proteins had highly improved DLS results and were able to concentrate well after exchanging buffers, and 9 have crystallized.

Figure 2A:
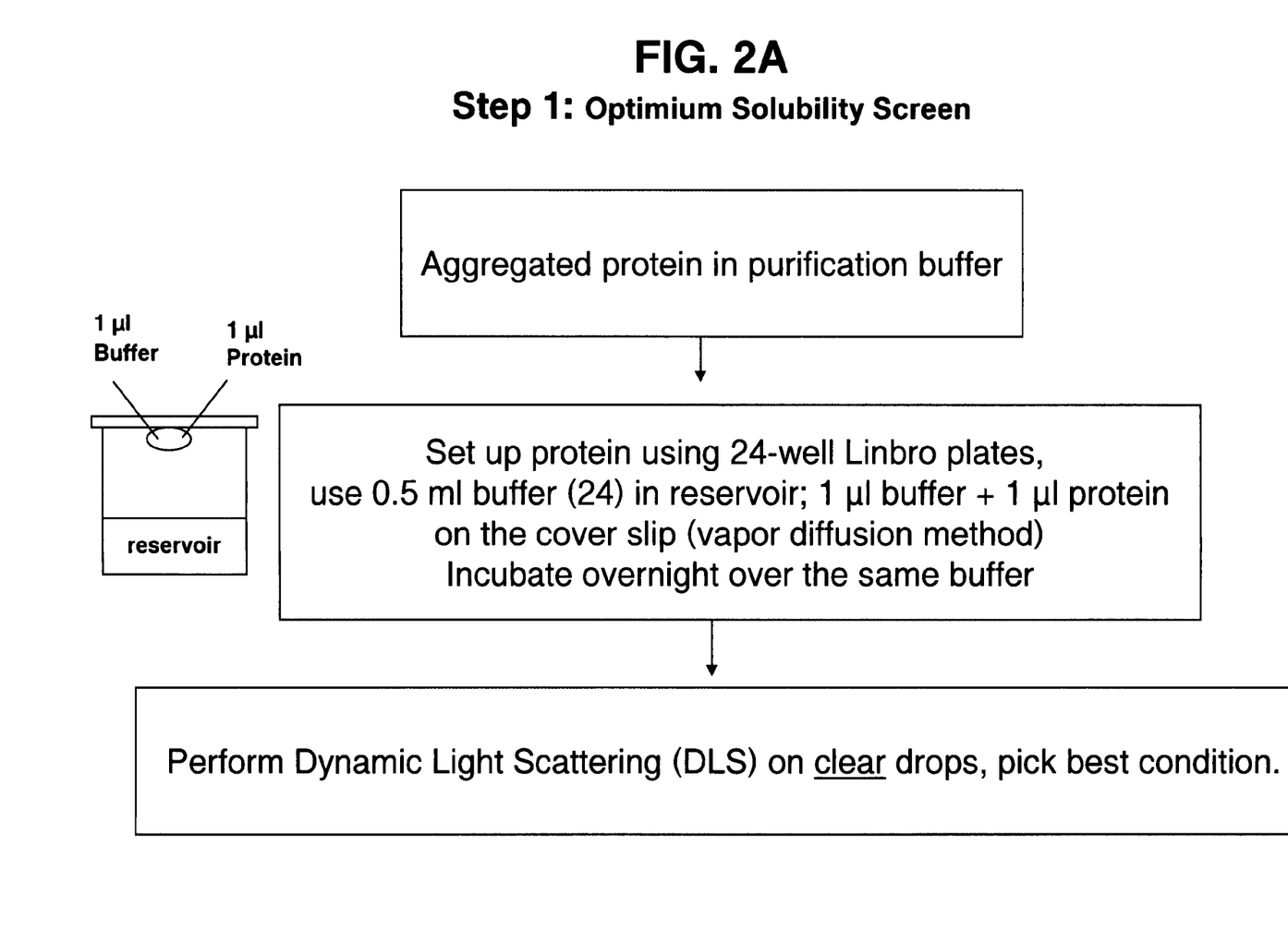
FIG. 2A is a flowchart showing the optimum solubility screen.
Figure 2B:
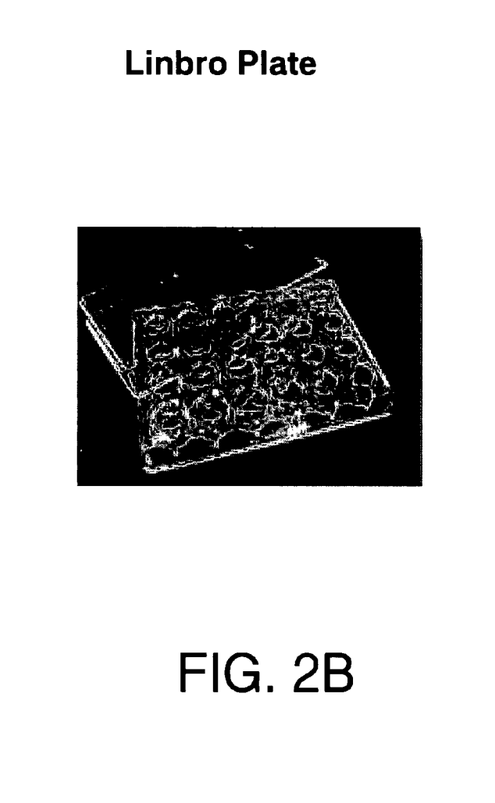
FIG. 2B shows the list of 24 screen buffers.
Figure 3:
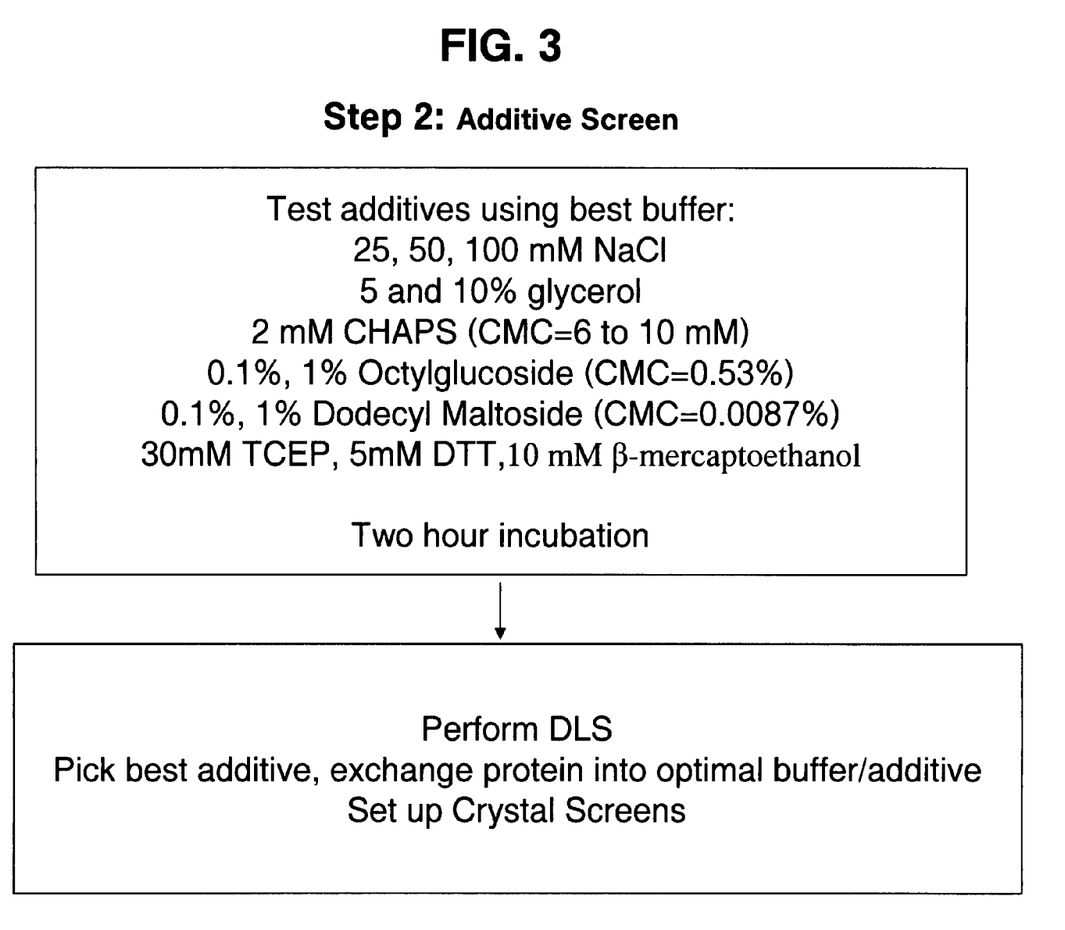
FIG. 3 is a flowchart showing the additive screen step.

Referring now to FIG. 2, one embodiment provides for a method for optimum solubility screening to crystallize proteins comprising the following steps: (1) providing a reservoir of purification buffer in a container, wherein the container has a cover slip; (2) depositing an aliquot of the buffer either on the cover slip or on a pedestal in the container above the buffer reservoir in each container; (2) placing a protein in the aliquot of buffer to form a protein solution drop; (4) inverting the cover slip onto the container; (5) incubating the container at a given temperature for a sufficient period of time; and (6) evaluating the protein solution drop for solubility and monodispersity. The method for screening is repeated or performed in parallel with a set of buffers for each protein provided in order to screen the optimal solubilization conditions.

Thus, the present invention further provides for a method to screen for optimum solubility condition to crystallize proteins comprising the following steps: (1) providing a multi-well container having at least 24 wells; (2) adding a reservoir of each of the set of 24 buffers in Table 1 to each well; (3) providing each well with a cover slip; (4) depositing on each cover slip a protein solution drop comprised of an aliquot of the protein and an aliquot of the same buffer in the well; (5) inverting the cover slips onto each respective well; (6) incubating the container at a given temperature for sufficient time; and (7) evaluating any clear protein solution drops to select the optimum solubility condition.

If the protein solution drop is clear but not monodisperse, i.e., drops without protein precipitation, an aliquot of an additive is added to each protein solution drop to find the best condition. The clear protein solution drops are evaluated to determine by DLS the monodispersity of the protein. Therefore, the method can further comprise the step of depositing an aliquot of an additive in the protein solution drop to help screen for the optimum solubility condition.

After screening for the optimum solubility condition, the target protein is then exchanged into the selected buffer and additive and can then be crystallized.

By the term "aggregating" it is meant, the protein cannot be concentrated or precipitates upon concentration. In a preferred embodiment, the amount of protein isolated and aggregated is sufficient for performing multiple screens to determine optimum detergents, re-folding and buffers.

The term "container" is meant to include any container suitable for performing the method of crystallization including depression wells and multi-well containers including containers such as an array plate, partitioned containers, and crystallization containers having a pedestal within each well. In a preferred embodiment, the container is a LINBRO plate as shown in FIG. 2B, having 24 wells.

In a preferred embodiment, a "reservoir" of buffer is an aliquot of about 0.1 to 1 mL of buffer deposited in each container. In a preferred embodiment, the aliquot of buffer is between 0.4 to 0.6 mL.

Parallel reactions can occur for several proteins. Therefore it is contemplated that multiple screens for different proteins can occur on a single multi-well plate having multiple containers or wells, e.g. 24, 64, 96, 384, or 1536 well plates.

In cases, where only a small amount of protein for crystallization is isolated, the set of buffers is comprised of at least 4, 5, 6, 8, 10, 12, 16 or 18 buffers, to insure that there are a sufficient number of buffers to represent a broad range of concentrations and pHs. It is preferred that the variety of buffers used in the screening set remain diverse, having at least 18 different buffers, although some buffers may be repeated within the set at different pHs. Most commercially available kits do not have such a broad range of buffers at such a broad range of pHs. Most provide about 5 buffers at varying concentrations or pHs.

In a preferred embodiment, the set of buffers is comprised of 24 buffers, wherein the buffers are at a concentration of 100 mM with a pH range from pH 3 to 10. It is contemplated that each buffer in the set of 24 buffers may be interchanged with other known and available buffers. In a preferred embodiment, the set of buffers is comprised of the 24 buffers listed in Table 1 shown below.

TABLE 1

List of optimum solubility screening buffers

| Number | Buffers (100 mM) | pH |
|---|---|---|
| 1 | Glycine | 3 |
| 2 | Citric Acid | 3.2 |
| 3 | PIPPS | 3.7 |
| 4 | Citric Acid | 4 |
| 5 | Sodium Acetate | 4.5 |
| 6 | Na K Phosphate | 5 |
| 7 | Sodium Citrate | 5.5 |
| 8 | Na K Phosphate | 6 |
| 9 | Bis Tris | 6 |
| 10 | MES | 6.2 |
| 11 | ADA | 6.5 |
| 12 | Bis Tris Propane | 6.5 |
| 13 | Cacodylate | 6.5 |
| 14 | Ammonium Acetate | 7 |
| 15 | MOPS | 7 |
| 16 | Na K Phosphate | 7 |
| 17 | HEPES | 7.5 |
| 18 | Tris | 7.5 |
| 19 | EPPS | 8 |
| 20 | Imidazole | 8 |
| 21 | Tris | 8.5 |
| 22 | CHES | 9 |
| 23 | CHES | 9.5 |
| 24 | CAPS | 10 |

Abbreviations used are as follows: ADA, N-(2-acetamido)-iminodiacetic acid; BME, β-mercaptoethanol; bis-tris, 2,2-bis(hydroxymethyl-2,2',2"-nitrilotriethanol; CAPS, 3-(cyclohexylamino)-1-propanesulfonic acid; CHAPS, [3-(3-cholamidopropyl)dimethylammonio]-1-propanesulfonate; CHES, 2-(cyclohexylamino)ethanesulfonic acid; DLS, dynamic light scattering; DTT, 1,4-dithio-DL-threitol; EPPS, 4-(2-hydroxyethyl)piperazine-1-propanesulfonic acid; HEPES, N-2-hydroxyethylpiperazine-N-2-ethanesulfonic acid; MES, 2-(N-morpholino)ethanesulfonic acid; MOPS, 3-(N-morpholino)propanesulfonic acid; PIPPS, 4-(2-hydroxyethyl)piperazine-1-propanesulfonic acid; Tris, [tris(hydroxymethyl)aminomethane]; TCEP, tris(2-carboxyethyl)phosphine.

In another embodiment, the invention provides for a kit supplied as a single, 24 or 96 deep well plate with the 24 unique buffer set of Table 1. Reagents are formulated using crystallization grade salts, polymers, buffers, organic solvents, and Type II analytical grade water. All reagents are sterile filtered into a sterile polypropylene 96 DeepWell Block and sealed. Complete instructions, formulations, and scoring sheet are supplied with the kit.

In another embodiment, the invention provides for a kit comprised of a set of vials or containers containing all 24 buffers formulated and ready for use in a crystallization plate. Sufficient volume of each buffer and additive is supplied to perform multiple screens of a protein target. The kit can further include vials or containers having the additives formulated and ready for use in the additive step of the method. Complete instructions, formulations and scoring sheet are supplied with the kit.

In a preferred embodiment, the cover slip for each container should act to seal the container to facilitate crystallization by the vapor diffusion method. Referring to FIG. 1, two methods are basically used for the vapor diffusion method: hanging drop method and the sitting drop method. In the present the protein solution drop is comprised of an aliquot of the buffer in the reservoir and an aliquot of the protein in the purification buffer. The protein solution drop is deposited either on the pedestal or on the cover slip to permit water to vaporize from the drop and transfer to the buffer in the reservoir, wherein the precipitant concentration increases to a level optimal for crystallization.

In one embodiment, an aliquot of about 0.1 μL to 2 μL of buffer and an aliquot of about 0.1 μL to 2 μL of aggregated protein in the purification buffer are both deposited on the cover slip to form a protein solution drop for hanging drop vapor diffusion. In a preferred embodiment, one protein solution drop is comprised of about 1 μL of buffer and 1 μL protein on the cover slip. In another embodiment, the protein solution drop is deposited on the pedestal.

After depositing the protein solution drop, the cover slips are inverted onto each of the containers, sealing each container. The containers are incubated at a given temperature for a sufficient period of time. In a preferred embodiment, the containers are incubated at room temperature for at least 24 hours. However, in other embodiments, the containers are incubated at other temperatures, for example, 4° C. The containers also may incubate for shorter or longer periods, e.g. several hours, several days, weeks or months or even up to one year, to promote protein crystallization. However, since the goal is high throughput screening of the optimum solubility conditions for each protein, an increased length of time may not be preferred.

After incubation, only the clear protein solution drops are evaluated to pick the best buffer condition. The drops that remained clear provide an indication that the protein sample is more soluble in those buffers. The clear drops are then diluted into the same reservoir solution, preferably at a ratio of 1:14 (protein:buffer). In a preferred embodiment, the clear drops are evaluated by Dynamic Light Scattering (DLS) for monodispersity. DLS measures the translational diffusion coefficient of a macromolecular undergoing Brownian motion in a solution. In essence, DLS measures the intensity of light scattered by molecules in solution. In turn, this measurement can tell you the size distribution of the protein molecules in solution. In a preferred embodiment, DLS is used to differentiate monodisperse solutions from polydisperse solutions. Homogeneous, non-aggregated monodisperse proteins have a high probability of producing crystals. Proteins with non-specific aggregates and heterogeneous samples are less likely to crystallize. DLS allows one to screen protein samples quickly, with small volumes of sample, at different temperatures. The procedure is non-invasive so the protein can be recovered. In another embodiment, if DLS is not an option one can obtain similar results using native polyacrylamide gel electrophoresis or size exclusion chromatography.

The protein is exchanged into the best buffer wherein the protein has the lowest radius and lowest polydispersity. In a preferred embodiment, an ideal monodisperse sample would have a monodispersity reading of radius<5 nm/polydispersity<25%. DLS can be performed using a DYNAPRO-99 (Wyatt Technology, Santa Barbara, Calif.) to assess the homogeneity/monodispersity of the sample. If the protein sample appears to be monodisperse in a particular buffer of the panel, then the protein should be exchanged into that buffer at a final concentration of 20 to 50 mM to conduct crystallization trials.

If none of the clear drops provided a monodisperse sample as required, i.e., having a radius<5 nm and polydispersity<25%, the buffer that provides the best DLS reading is selected and an additive screen can then be tested. In a preferred embodiment, the protein sample is exchanged into the best buffer from the 24-buffer screen to a final concentration of at least 2-3 mg/ml. Individual additives can be added to the protein sample. After incubation at a given temperature (e.g., room temperature), DLS readings are performed. In one embodiment, based on the protein's properties, the target is exchanged into the selected buffer(s) and appropriate additives. In another embodiment, 13 wells contain the target in the best of the 24-buffers and one of each of the additives is added to each well. In a preferred embodiment, the individual additives shown in Table 2 can be added to the protein sample. The additives shown are the final concentrations of additives to be used in a final volume.

TABLE 2

Preferred Additives (Final Concentration)

25 mM sodium chloride
50 mM sodium chloride
100 mM sodium chloride
5% glycerol
10% glycerol
2 mM CHAPS (CMC = 6 to 10 mM)
0.1% Octylglucoside (CMC = 0.53%)
1% Octylglucoside (CMC = 0.53%)
0.1% Dodecyl Maltoside (CMC = 0.0087%)
1% Dodecyl Maltoside (CMC = 0.0087%)
10 mM BME
1 mM DTT
5 mM DTT
30 mM TCEP By adding additives, an 78% success rate (i.e., crystallization) was obtained where DLS was improved in 11 out of 14 tested proteins by exchanging the buffer. Nine of the eleven proteins were able to produce crystals of varying qualities.

EXAMPLE 1

Protein 1371B and Other Proteins Crystallized by the Method

Figure 4:
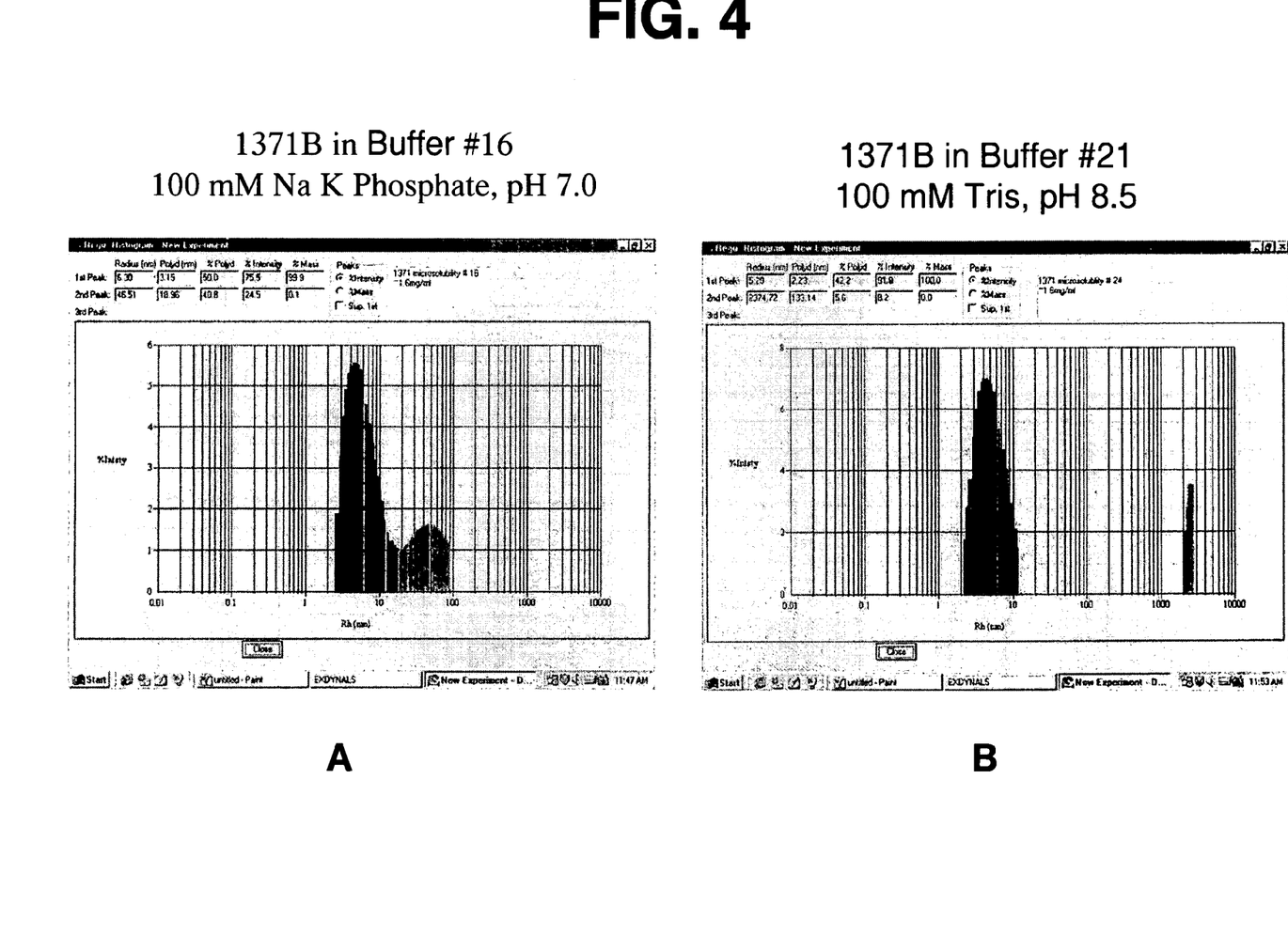
FIG. 4 is a chart showing a comparison between Dynamic light scattering scans of protein 1371B in different OS screen buffers. (a) Protein in 100 mM Na K Phosphate, pH 7.0, (b) Protein in 100 mM Tris-HCl, pH 8.5, (c) Protein in 100 mM Tris-HCl, pH 8.5, 1% Octylglucoside, (d) The buffer for 1371B was exchanged to 20 mM Tris-HCl, pH 8.5, 1% Octylglucoside, crystals were obtained from 0.1 M Sodium Acetate, pH 4.6, 6.0 M Ammonium Nitrate and the structure was solved (unpublished results).

The OS screen has been performed on 14 samples that had aggregated as measured by DLS, had precipitated upon concentration or could not be concentrated. One of the proteins, his-tagged 1371B, was purified through a metal chelating column (HiTrap Chelating HP, Piscataway, N.J.) and Superdex 75 size exclusion chromatography (Piscataway, N.J.) column. The sample (20 mM Tris-HCl, pH 7, 0.3 M NaCl) could be concentrated to 27 mg/ml only upon removal of salt but the DLS showed high polydispersity. The protein underwent OS screen and some of the drops remained clear. But as shown in FIGS. 4a and 4b, although both buffers #16 and 21 gave a clear drop, the sample was more monodisperse in Tris-HCl, pH 8.5, buffer. Even in this buffer, one could observe a higher molecular weight peak, so the Additive Screen was tested and 1% octylglucoside was shown to make the 1371B sample more monodisperse with a radius of 3.15 nm and 21% polydispersity. The buffer was exchanged to 20 mM Tris-HCl, pH 8.5, 1% octylglucoside (FIG. 4c), and crystallization screens were performed. The protein crystallized (FIG. 4d) and the structure was determined (unpublished results).

Table 3 lists 14 protein samples that have been screened through the OS screen. These proteins varied in molecular weight over a wide range.

TABLE 3

Optimization Results

| Protein ID | Molecular weight (kDa)/pI[#] | DLS after purification (nm[+]/PD[§])/purification buffer | DLS in best buffer (nm[+]/PD[§])/best buffer | Additive | Crystals |
|---|---|---|---|---|---|
| 1008B | 34.9/9.1 | Protein precipitated during concentration/Tris pH 7.5 | Precipitation in all drops | | No |
| 1135B | 59.8/5.9 | 7.6/35%; protein precipitated during concentration/HEPES pH 8.0 | 5.8/9%/PIPPS pH 3.7 | | Yes[##] |
| 1139B | 16.7/6.7 | 6.1/37%/Tris pH 8.0 | 4.2/27%/MES pH 6.5 | 5% glycerol | Yes |
| 1142B | 16.8/6.8 | 39/19.3%; protein precipitated/HEPES pH 8.0 | 4.9/20%/sodium acetate pH 5.0 | 50 mM NaCl, 1% OG, 0.1 M TCEP | Yes |
| 1149B | 10.8/9.2 | 7.36/66%/HEPES pH 7.0 | 3.5/15%/potassium phosphate pH 5.0 | | Yes |
| 1154B | 24.9/8.5 | 8.8/53%/HEPES pH 7.5 | 3.41/13.8%/potassium phosphate pH 7.5 | | No |
| 1166B | 30.1/4.9 | Protein aggregated with time/Tris pH 7.5 | No good buffer found | | No |
| 1227B | 35.6/6.8 | Protein precipitated during concentration/HEPES pH 8.0 | Crystallized in OS screen/MES pH 6.2 | | Yes[##] |
| 1275B | 44.1/6.4 | Could not read the DLS/HEPES pH 8.0 | 3.78/28%/MES pH 6.0 | | Yes |
| 1334B | 59.9/4.3 | 11.6/45%/HEPES pH 7.0 | 5.1/14%/HEPES pH 7.5 | | No |
| 1335B | 53.5/4.6 | 19/46%/HEPES pH 7.0 | No good buffer found | | No |
| 1349B | 23.1/9.1 | 2.05/8.6%, part of large aggregate/HEPES pH 7.5 | Crystallized in OS screen/MES pH 5.8 | | Yes[##], solved |
| 1368B | 24.6/6.3 | 4.22/58%/Tris pH 7.5 | 3.9/12%/sodium acetate pH 5.0 | 25 mM NaCl | Yes |
| 1371B | 27.1/5.3 | Too aggregated/Tris pH 7.0 | 3.15/21%/Tris pH 8.5 | 0.1% OG | Yes, solved |

[#]pI, isoelectric point.
[+]nm, hydrodynamic radius in nanometers.
[§]PD, polydispersity.
[##]Protein crystallized while performing the OS screen.

Using conventional methods, these proteins aggregated, precipitated or had non-ideal DLS results. The OS screen indicated that out of the 14 protein samples, the DLS of 11 of them could be improved by exchanging the buffer and in some cases an additive further improved DLS. Nine of these proteins could be crystallized. It is also interesting to note that in three cases (targets 1135B, 1227B, and 1349B) the proteins crystallized while OS screen was performed. Crystals were improved by testing different size polyethylene glycols (400, 1500, 3350, 4000, 8000 daltons) as precipitants with the particular buffer that was selected as being the optimum one for solubility with the protein left in the original buffer. This allowed for much more improved crystals.

TABLE 4

Summary of Optimum Solubility Screen Results

| Number of Targets Tested | Number of Targets where DLS was Improved by Exchanging the Buffer | Number of Targets that Crystallized |
|---|---|---|
| 14 | 11 (78%) | 9 (64%) |

EXAMPLE 2

Preparation of Protein Samples

The proteins that we have worked on are expressed from genes from *Mycoplasma pneumoniae, M. genitalium* or their homologs from other organisms. The protein identification numbers listed on Table 3 are targets from the BSGC website. These proteins have a $his_6$ tag or a $his_6$-Maltose Binding Protein (MBP)-Tobacco Etch Virus (TEV) protease cleavage site at the N-terminus. Purification for the proteins with a $his_6$ tag involved an immobilized metal affinity column (IMAC) followed by either ion-exchange chromatography and/or size exclusion chromatography. For those proteins with a $his_6$-MBP fusion, a TEV cleavage step was included in the purification protocol after the IMAC step.

EXAMPLE 3

Optimum Solubility (OS) Screen

A set of 24 buffers at a concentration of 100 mM with a pH range from 3 to 10 was prepared using Fluka chemicals (Table 1). The screening was done by pipetting 0.5 ml of each of the buffers into each reservoir of a 24-well Linbro plate. A 1 µl aliquot of protein solution (concentrated to as high a concentration as possible) was pipetted onto a siliconized glass cover slip and to it was added 1 µl of 100 mM reservoir buffer. A layer of silicone grease was applied to the top of each of the wells and the cover slips were then inverted and sealed onto each of the wells. The plates were incubated at room temperature for 24 hrs. During this period vapor diffusion takes place and depending on the stability of the protein in a given buffer, one can observe under a light microscope clear drops or drops with different degrees of precipitation. The protein concentration ranged from 3.0 mg/ml to 30 mg/ml.

EXAMPLE 4

Dynamic Light Scattering (DLS) Analysis

The drops that remained clear gave us an indication that the protein sample was more soluble in those buffers. The clear drops were then diluted into the same reservoir solution at a ratio of 1:14 (protein:buffer) and DLS was performed using a DynaPro-99 (Wyatt Technology, Santa Barbara, Calif.) to assess the homogeneity/monodispersity of the sample. If the protein sample appeared to be monodisperse in a particular buffer, then the protein was exchanged into that buffer at a final concentration of 20 mM.

EXAMPLE 5

Additive Screen

If none of the clear drops provided an ideal monodisperse sample (radius<5 nm/polydispersity<25%), the buffer that gave the best DLS reading was selected and an additive screen was tested. The protein sample was exchanged into the best buffer from the OS screen using an Ultrafree unit (Millipore Corp., Bedford, Mass.) to a final concentration of at least 2-3 mg/ml. In 0.5 ml microfuge tubes, individual additives were added to 15 µl of protein sample (Table 2 or Table 6). After 2 hr incubation at room temperature, DLS readings were performed. The condition that gave the best DLS reading was selected and the protein was exchanged into the selected buffer and additive before setting up the crystal screens. See the results shown in Table 3.

EXAMPLE 6

Optimum Solubility Screen Assay Standard Operating Procedure

The following is the Standard Operating Procedure used by the Berkeley Structural Genomics Center when implementing the method in their high throughput facility. The materials used are VDX 24 well plate (#HR3-140, Hampton Research, Aliso Viejo, Calif.), glass cover slips (#HR3-211, Hampton Research), and Cryschem Plate (sitting drop) (#HR3-158, Hampton Research). The reagents are the 24 buffers in Table 1, used at 0.1M concentration. All buffers are made using chemicals from Fluka, Calbiochem, and Research Organics. The buffers are filter sterilized and stored at 4° C. except for Buffer #3 (PIPPS) which must be stored at room temperature. The recipes for each buffer are found in Table 5 below. Buffers are prepared as 1 M Stock Solutions except for Buffer #3. Working solutions are used as 0.1 M solutions. Buffers are kept at 4 C except for Buffer #3.

TABLE 5

Recipes for Buffers for Optimum Solubility Screen

| | Buffer(1M) | pH | Vendor | Recipe for 50 mL, 1 M Stock Solutions |
|---|---|---|---|---|
| 1 | Glycine | 3 | Fluka | 3.75 g Glycine |
| 2 | Citric Acid | 3.2 | Fluka | 9.62 g citric acid |
| 3 | PIPPS | 3.7 | Calbiochem | 8.26 g PIPPS = 0.5 M, keep at room temperature. |
| 4 | Citric Acid | 4 | Fluka | 9.62 g citric acid |
| 5 | Sodium acetate | 4.5 | Fluka | 4.10 g sodium acetate |
| 6 | Na K phosphate | 5 | Fluka | 6.80 g $H_2KO_4P$ + 6.0 g $H_2NaO_4P$ |
| 7 | Sodium citrate | 5.5 | Fluka | 14.7 g sodium citrate |
| 8 | Na K phosphate | 6 | Fluka | 6.80 g $H_2KO_4P$ + 6.0 g $H_2NaO_4P$ |
| 9 | Bis Tris | 6 | Fluka | 10.46 g Bis Tris |
| 10 | MES | 6.5 | Fluka | 10.66 g MES |

TABLE 5-continued

Recipes for Buffers for Optimum Solubility Screen

| Buffer(1M) | | pH | Vendor | Recipe for 50 mL, 1 M Stock Solutions |
|---|---|---|---|---|
| 11 | ADA | 6.5 | Fluka | 9.5 g ADA + ~5 ml 10M NaOH + H$_2$O up to 50 ml |
| 12 | Bis Tris Propane | 6.5 | Fluka | 14.12 g Bis Tris Propane |
| 13 | Cacodylate | 6.5 | Fluka | 10.7 g Na Cacodylate |
| 14 | Ammonium acetate | 7 | Fluka | 3.85 g Ammonium acetate |
| 15 | MOPS | 7 | Sigma | 10.46 g MOPS |
| 16 | Na K phosphate | 7 | Fluka | 6.80 g H$_2$KO$_4$P + 6.0 g H$_2$NaO$_4$P |
| 17 | HEPES | 7.5 | Fluka | 13.02 g HEPES |
| 18 | TRIS | 7.5 | Sigma | 6.055 g TRIS Base |
| 19 | EPPS | 8 | Fluka | 12.62 g EPPS |
| 20 | Imidazole | 8 | Research Organics | 33.3 ml 1.5M stock Imidazole + H$_2$O up to 50 ml |
| 21 | TRIS | 8.5 | Sigma | 6.055 g TRIS Base |
| 22 | CHES | 9 | Fluka | 10.36 g CHES |
| 23 | CHES | 9.5 | Fluka | 10.36 g CHES |
| 24 | CAPS | 10 | Fluka | 11.06 g CAPS |

The screen also requires a DLS instrument, such as Dyna Pro 99 Dynamic Light Scattering instrument (Wyatt Technology Corporation, Santa Barbara, Calif. 1-805-681-9009). The purpose of the Optimum Solubility Screen is to try to find a buffer that will disaggregate the protein of interest. This assay is for proteins that cannot be concentrated and/or have poor DLS data.

The procedure is as follows to perform buffer screening: (1) Get the protein as concentrated as possible. Protein sample should be at least 10 mg/ml. (2) Grease a 24 VDX 24 well plate. (3) Aliquot 500 µl of each buffer (0.1 M concentration) to the wells. Buffer #1 in well 1, buffer #2 in well 2, etc. (4) Place a glass cover slip on a dark surface for better visibility. Pipette 1 µl of buffer #1 from the reservoir on the glass cover slip. (5) With a new pipette tip, add 1 µl of your protein sample to the buffer drop. (6) Flip over the glass cover slip and firmly apply onto the corresponding greased buffer well plate. Be careful not to break the glass cover as you place it onto the plate. (7) Repeat steps 4-6 for all 24 wells. (7 a) If the protein cannot be concentrated to 10 mg/ml, use a sitting drop plate, then place 7 µl of protein+7 µl of buffer onto the post of a Cryschem Plate (Hampton HR3-158), add 500 µl of reservoir into the well. After overnight incubation at room temperature, collect all 14 µl and read in DLS instrument. (8) Let the plate incubate overnight at room temperature. (9) Observe the clarity of the drops under a microscope and score each drop on the OSS data sheet as follows: C=clear drops; P=precipitated drops. (10) Select conditions that are absolutely clear and perform DLS on those conditions. Take the drop (<2 µl) and add the corresponding buffer [14 µl] to generate a DLS sample of 15 µl. You want the final protein concentration of the DLS sample to be 1-2 mg/ml (the minimum concentration to obtain accurate results is 1 mg/ml) and the minimum volume of the sample is 15 µl. (11) Save the 24 well plate for the next OSS. Do not discard the old glass slips until you need the plate again to eliminate buffer evaporation. When reusing, just re-grease the plate and use new glass cover slips. The 24 well plate can be reused ONE TIME ONLY. (12) From the DLS data, select the best buffer condition giving the smallest radius (<5 nm), lowest polydispersity (<30%) and highest intensity when doing DLS measurement. After the protein has been placed in the new buffer, concentrate it and set up crystallization trials.

If conditions are not optimal after performing the initial buffer screening, proceed to use additives. At final concentration, common additives used are 5% glycerol, 10% glycerol, 25, 50, and 100 mM NaCl, 0.1%, 1% octylglucoside, 10 mM betamercaptoethanol, 5 mM dithiothreitol, 2 mM CHAPS. The procedure is as follows to perform additive screening: (A) Use only enough protein to test for the additives. Calculate how much protein needed: # of additives×protein (2 mg/ml)×20 µl. Estimate some loss during concentration and use this amount to exchange the protein into the best buffer condition found above (Step 12) at a concentration of 50 mM. Use a concentrator (Apollo, Ultrafree, etc.) to concentrate the protein: (a) add the selected buffer to the protein (1:5 dilution, invert gently), concentrate down; (b) add more buffer (1:5 dilution) concentrate again; (c) repeat step (b) one more time. Alternatively the protein can be dialysed against the selected buffer and then concentrated to 2 mg/ml. (B) Based on the protein's properties, decide which additives are going to be tested with the selected buffer (e.g., if it has cysteines it may be preferable to use betamercaptoethanol or dithiothreitol). (C) The total volume of the sample to be 15-20 µl and the protein concentration to be 1-2 mg/ml. Place 15-20 µl of protein (1-2 mg/ml) in 0.5 ml eppendorf tubes and add stock additives to each of the tubes to desired concentration. Mix gently by pipetting up and down. (D) Let these samples incubate for 30-60 minutes at room temperature, but preferably overnight. (E) Spin the samples in a microfuge for 5 min and perform DLS on each sample, compare to the results from Step 12, and determine the optimal condition. (F) The optimal buffer with the best additive is then used to exchange the protein using a concentrator as indicated in Step A. Crystallization trials are then performed.

TABLE 6

List of Additives (final concentration):

10 mM BME
2 mM CHAPS
5 mM DTT
5% glycerol
10% glycerol
25 mM NaCl
50 mM NaCl
100 mM NaCl
0.1% Octylglucoside
1.0% Octylglucoside The present embodiments, examples, methods, and procedures are meant to exemplify and illustrate the invention and should in no way be seen as limiting the scope of the invention. Variations in the compositions, buffers, additives and their concentrations and various modifications of the methods and applications thereof of the invention will be apparent to those skilled in the art without departing from the scope and spirit of the invention.

Any patents or publications mentioned in this specification are indicative of levels of those skilled in the art to which the invention pertains and are hereby incorporated by reference to the same extent as if each was specifically and individually incorporated by reference.

REFERENCES

D'Arcy, A. (1994). *Acta Cryst.* D50, 469-471.
Ferre-D'Amare, A. R. & Burley, S. K. (1997). Methods Enzymol. 276, 157-166.
Habel, J. E., Ohren, J. F.& Borgstahl, G. E. O. (2001). Acta Cryst. D57, 254-259.

Jancarik, J. & Kim, S.-H. (1991). *J. Appl. Cryst.* 24, 409-411.
Laemmli, U. K. (1971). *Nature* (London), 22, 680-685.
LePre, C. A. & Moore, J. M. (1999). *Journal of Biomolecular NMR,* 12, 493-499.
Zulauf, M. & D'Arcy, A. (1992). *J. Cryst. Growth,* 122, 102-106.

What is claimed is:

1. A method of screening for an optimal buffer solution for crystallizing at least one protein comprising:
   (a) filling a plurality of microwell reservoirs on a microwell plate each with a test buffer, each microwell having a cover, and wherein the test buffers consisting of the set of 24 test buffers shown here in Table 1,

| Number | Buffers (100 mM) | pH |
|---|---|---|
| 1 | Glycine | 3 |
| 2 | Citric Acid | 3.2 |
| 3 | PIPPS | 3.7 |
| 4 | Citric Acid | 4 |
| 5 | Sodium Acetate | 4.5 |
| 6 | Na K Phosphate | 5 |
| 7 | Sodium Citrate | 5.5 |
| 8 | Na K Phosphate | 6 |
| 9 | Bis Tris | 6 |
| 10 | MES | 6.2 |
| 11 | ADA | 6.5 |
| 12 | Bis Tris Propane | 6.5 |
| 13 | Cacodylate | 6.5 |
| 14 | Ammonium Acetate | 7 |
| 15 | MOPS | 7 |
| 16 | Na K Phosphate | 7 |
| 17 | HEPES | 7.5 |
| 18 | Tris | 7.5 |
| 19 | EPPS | 8 |
| 20 | Imidazole | 8 |
| 21 | Tris | 8.5 |
| 22 | CHES | 9 |
| 23 | CHES | 9.5 |
| 24 | CAPS | 10 |

(b) depositing a protein and a droplet of each of said buffers either on the cover or on a pedestal above the microwell reservoir in each microwell to form a protein solution droplet, wherein the test buffer in the droplet and the test buffer in the reservoir are the same,
   (c) covering each microwell with the cover,
   (d) incubating the plate at a temperature for conducting vapor dispersion of said protein solution droplet over a period of time,
   (e) detecting microwells having clear protein solution droplets, wherein test buffers yielding clear protein solution droplets identify a buffer having solubility for the protein,
   (f) evaluating any clear protein solution droplets for monodispersity in order to select the optimum solubility condition to crystallize the protein, wherein said clear protein solution droplets are protein solution droplets without any protein precipitation and wherein monodispersion is a droplet having a radius<5 nm and polydispersity<25%, whereby the evaluation comprising:
      (1) selecting the test buffers having said clear protein solution droplets,
      (2) conducting dynamic light scattering (DLS) analysis of a solution in a reservoir, the solution comprising a ratio of protein to test buffer of about 1 to about 14,
      (3) detecting monodispersion of the protein in said reservoir using DLS;
      (4) identifying test buffers having clear droplets but poor monodispersion, as determined by DLS, for further testing with an additive to optimize monodispersion of the protein in the test buffer, the additive testing comprising:
         (A) adding a test additive to the test buffer solution in said reservoir, the test additive selected from a plurality of test additives, the test buffer solution having an amount of protein in a range from about 2 to about 3 mg of protein,
         (B) detecting monodispersion of the protein in the buffer additive solution using DLS, and
         (C) comparing a monodispersion of the protein with the additive in the buffer solution with monodispersion of the protein in buffer alone to determine whether to use the additive in the solution, and
   (g) selecting the optimal test buffer and any additive solution for crystallizing at least one protein, wherein the optimal buffer is the buffer wherein the protein has the lowest radius and lowest polydispersity which thereby indicates an optimal buffer solution for crystallizing the protein.

2. The method of claim 1, wherein if the protein solution droplets are not clear, steps a through f are repeated with the buffer which showed the lowest monodispersity, wherein step (b) further comprising step (b.1) adding an aliquot of an additive to said protein solution droplets to find the best condition, wherein the additives consisting of the additives of: 10 mM BME, 2 mM CHAPS, 5 mM DTT, 5% glycerol, 10% glycerol, 25 mM NaCl, 50 mM NaCl, 100 mM NaCl, 0.1% Octylglucoside, or 1.0% Octylglucoside.

3. The screening method of claim 1, wherein the protein in each of said droplets has a concentration of at least 3 mg/ml, the droplets having volumes of about 2 μL.

4. The screening method of claim 1, further comprising using the buffer recipes listed in the table below for forming the test buffers,

| | Buffer (1M) | pH | Recipe for 50 mL, 1M Stock Solutions |
|---|---|---|---|
| 1 | Glycine | 3 | 3.75 g Glycine |
| 2 | Citric Acid | 3.2 | 9.62 g citric acid |
| 3 | PIPPS | 3.7 | 8.26 g PIPPS = 0.5M, keep at room temperature. |
| 4 | Citric Acid | 4 | 9.62 g citric acid |
| 5 | Sodium acetate | 4.5 | 4.10 g sodium acetate |
| 6 | Na K phosphate | 5 | 6.80 g $H_2KO_4P$ + 6.0 g $H_2NaO_4P$ |
| 7 | Sodium citrate | 5.5 | 14.7 g sodium citrate |
| 8 | Na K phosphate | 6 | 6.80 g H2KO4P + 6.0 g H2NaO4P |
| 9 | Bis Tris | 6 | 10.46 g Bis Tris |
| 10 | MES | 6.5 | 10.66 g MES |
| 11 | ADA | 6.5 | 9.5 g ADA + ~5 ml 10M NaOH + H2O up to 50 ml |
| 12 | Bis Tris Propane | 6.5 | 14.12 g Bis Tris Propane |
| 13 | Cacodylate | 6.5 | 10.7 g Na Cacodylate |
| 14 | Ammonium acetate | 7 | 3.85 g Ammonium acetate |
| 15 | MOPS | 7 | 10.46 g MOPS |
| 16 | Na K phosphate | 7 | 6.80 g H2KO4P + 6.0 g H2NaO4P |
| 17 | HEPES | 7.5 | 13.02 g HEPES |
| 18 | TRIS | 7.5 | 6.055 g TRIS Base |
| 19 | EPPS | 8 | 12.62 g EPPS |
| 20 | Imidazole | 8 | 33.3 ml 1.5M stock Imidazole + H2O up to 50 ml |
| 21 | TRIS | 8.5 | 6.055 g TRIS Base |
| 22 | CHES | 9 | 10.36 g CHES |
| 23 | CHES | 9.5 | 10.36 g CHES |
| 24 | CAPS | 10 | 11.06 CAPS. |

5. The screening method of claim 1, wherein the test additives are selected from 10 mM BME, 5% glycerol, 10% glycerol, 25 mM NaCl, 50 mM NaCl, 100 mM NaCl, 2 mM CHAPS where CMC=6 to 10 mM, 0.1% Octylglucoside where CMC=0.53%, 1% Octylglucoside where CMC=0.53%, 0.1% Dodecyl Maltoside where CMC=0.0087%, 1% Dodecyl Maltoside where CMC=0.0087%, 1 mM DTT, 5 mM DTT, and 30 mM TCEP.

* * * * *